United States Patent [19]

Shioya et al.

[11] Patent Number: 5,035,893

[45] Date of Patent: Jul. 30, 1991

[54] WOUND COVERING

[75] Inventors: Nobuyuki Shioya, Yokohama; Yoshimitsu Kuroyanagi, Hachioji; Yasuo Kounami; Tatsuhiko Kobayashi, both of Sagamihara, all of Japan

[73] Assignee: Mitsubishi Kasei Corporation, Tokyo, Japan

[21] Appl. No.: 440,197

[22] Filed: Nov. 22, 1989

[30] Foreign Application Priority Data

Nov. 29, 1988 [JP] Japan ................................ 63-301856

[51] Int. Cl.$^5$ ........................ A61F 13/02; A61K 9/70; A61L 15/03; A61L 15/06
[52] U.S. Cl. ................................... 424/447; 424/443; 424/445; 424/484; 424/485; 424/488
[58] Field of Search ............... 424/443, 445, 447, 484, 424/485, 488

[56] References Cited

U.S. PATENT DOCUMENTS 4,590,022  5/1986  Cioca et al. .................... 428/423.1

FOREIGN PATENT DOCUMENTS 0184233 11/1986 European Pat. Off. ............ 424/445
63-59706 11/1988 Japan .

*Primary Examiner*—Merrell C. Cashion, Jr.
*Assistant Examiner*—Carlos Azpuru
*Attorney, Agent, or Firm*—Oblon, Spivak, McClelland, Maier & Neustadt

[57] ABSTRACT

The present invention relates to a wound covering comprising a sheet of biopolymeric material and a film of a polyurethane resin obtained by reacting a diisocyanate and a random copolymer of tetrahydrofuran and ethylene oxide to produce a urethane prepolymer, and extending the molecular chain of said prepolymer by using a chain extender, said random copolymer containing 20 to 80% by weight of the ethylene oxide unit in the molecular chain thereof and having a number-average molecular weight of 800 to 3000.

The wound covering of the present invention is excellent in adhesion flexibility, durability, easy handling, preservation, sterile filtration, compatibility with cell, blood starching, water-vapor permeability. Therefore, it is quite suitable for practical use.

13 Claims, No Drawings

WOUND COVERING

BACKGROUND OF THE INVENTION

This invention relates to wound coverings.

In particular, it relates to the wound coverings which comprise two layers, one is a polyurethane resin film which has good moisture permeability, and the other is a sheet of biopolymeric materials, which is effective for growth of tissue cell as an artificial skin.

The properties necessary to wound coverings are 1) adhesion, 2) flexibility, 3) durability, 4) easy handling, 5) preservation, 6) sterile filtration, 7) compatibility with cells, 8) blood stanching, 9) water-vapor permeability and so on.

However, it is the defect for the conventional wound coverings that they satisfy some properties, but they do not satisfy the other properties among those described above.

For example, a sheet consisted of only biopolymeric materials almost lacks flexibility and sterile filtration. In the case of worse flexibility, the sheet lacks adhesion property at a wound surface, and some of such sheets almost lack preservation property, and cannot be handled easily. And also in the case of worse sterile filtration, it is necessary to apply cream containing antibacterial agent every 2 or 3 days to diseased part. This work is very troublesome for nurse and very painful for patient.

On the other hand, a laminated sheet of a biopolymeric material sheet and a silicone film has a poor water-vapor permeability, and is in danger to store exudate under the covering. It is possible to make such a laminated sheet thinner in order to improve these defects. But, a thinner sheet lacks easy handling.

Generally, a lot of exudate is generated at the first stage of using of a wound covering. A laminate sheet is used to be made holes mechanically in it in order to drain the exudate. But, when the generation of the exudate becomes little, the holes are clogged by solidification of the exudate. Therefore, after the clogging of the holes, the sheet is necessary to have good water-vapor permeability. For example, in the case of a burn injury, water-loss by evaporation from a wound is stated to be 300 g $H_2O/m^2 \cdot 24$ hrs in the first degree burn, 4300 g $H_2O/m^2 \cdot 24$ hrs in the second degree burn, 3400 g $H_2O/m^2 \cdot 24$ hrs in the third degree burn. (L. O. Lamke Burns. 3 p 159-165).

A silicone-resin film used as a wound covering, for example, does not have sufficient property of water-vapor permeability, because of its low value of water-vapor permeability, 1000 1700 $H_2O/m^2 \cdot 24$ hrs. Therefore, wound covering has not been provided until now, which has a water-vapor permeability sufficient for a large amount of evaporation mentioned above in addition to good flexibility, durability, and easy handleability.

The present inventors have made studies for solving the problems in the conventional sheet which consists of only biopolymeric materials and laminate sheet thereof, i.e., for providing a wound covering which is excellent in 1) adhesion, 2) flexibility, 3) durability, 4) easy handling, 5) preservation, 6) sterile filtration, 7) compatibility with cells, 8) blood stanching as well as 9) water-vapor permeability. As a result of the studies, the present inventors have found that a laminate comprising a specific polyurethane film and a sheet of biopolymeric materials is sufficient for the purpose, and based on this finding the present invention has been accomplished.

SUMMARY OF THE INVENTION

In an aspect of the present invention, there is provided a wound covering comprising a sheet of biopolymeric material and a film of a polyurethane resin obtained by reacting a diisocyanate and a random copolymer of tetrahydrofuran and ethylene oxide to produce a urethane prepolymer, and extending the molecular chain of said prepolymer by using a chain extender, said random copolymer containing 20 to 80% by weight of the ethylene oxide unit in the molecular chain thereof and having a number-average molecular weight of 800 to 3000.

DETAILED DESCRIPTION OF THE INVENTION

The polyurethane resin used for the polyurethane film in the present invention is obtained by using a random copolymer of tetrahydrofuran (hereinafter referred to as "THF") and ethylene oxide (hereinafter referred to as "EO") as the polyol component. This copolymer is synthesized by ring-opening copolymerization of THF and EO at temperature of 20 to 50° C, in the presence of an initiator, for example, water, short-chain diols such as ethylene glycol, 1,4-butane diol, and Lewis acid-catalyst such as boron trifluoride ethyl etherate.

The content of the EO unit in the random copolymer of THF and EO is 20 to 80 weight %, preferably 30 to 70 weight %, more preferably 40 to 60 weight % based on the copolymer in order to reduce swelling by absorbing water and lowering in physical properties of the polyurethane film. The number-average molecular weight of the random copolymer of THF and EO is 800 to 3000. If the number-average molecular weight is less than 800, the polyurethane film becomes hard, and if more than 3000, it shows large tacky adhesion and increase of swelling by absorbing water. In order to provide excellent film properties, the number-average molecular weight is preferably in the range of 1000 to 2500.

A mixture of the random copolymer of THF and EO and polytetramethylene ether glycol (hereinafter referred to as "PTMG") can also be used in case of necessity. In this case, the number-average molecular weight of PTMG to be added is 800 to 3000, and that of the polyol mixture is 800 to 3000, preferably 1000 to 2500 in order to provide a well balanced properties.

There is no disadvantage to the present invention, if the above random copolymer of THF and EO includes a partial block-copolymer-structure in its molecular chain.

The copolymer of THF and EO generally includes the block copolymer which is synthesized by addition reaction of EO and PTMG obtained from the ring-opening polymerization of THF, or addition reaction of THF and polyethylene glycol (hereinafter referred to as "PEG") obtained from ring-opening polymerization of EO. However, polyurethane produced from these block copolymers is not suitable for practical use, because the increase of swelling by absorbing water is remarkable with the increase of EO content, similar to the case of using a mixture of PTMG and PEG, due to including the hydrophilic homopolymer long-chain of EO in a mclecular chain.

When the above random copolymer of THF and EO, or the mixture of this random copolymer and PTMG is used as the polyol component of a polyurethane, the polyurethane film shows good water vapor permeability in comparison with the case that the above block copolymer of THF and EO is used, or that a mixture of PTMG and PEG are used together, though the increase of the water absorption with increase of the content EO unit is small.

In order to obtain the polyurethane resin used in the present invention, in general, is used a method wherein after obtaining urethane prepolymer having isocyanato group at the end of its molecular chain by reacting the above specific polyol component and an excess equivalent of diisocyanate at 70 to 120° C, the chain of the urethane prepolymer is extended by a chain extender at 20 to 100° C in organic solvent.

The equivalent ratio of diisocyanate and polyol component in urethane prepolymer is usually 1.5 to 6:1, and preferably 1.8 to 4.5:1, for providing good physical properties and water-vapor permeability.

The isocyanates used in the present invention are, for example, aromatic diisocyanates such as 4,4'-diphenylmethane diisocyanate, 2,4- and 2,6-tolylene diisocyanate, 1,5- naphthalene diisocyanate, m- and p-phenylenediisocyanate, alicyclic diisocyanates such as isophorone diisocyanate, 4,4'-dicyclohexylmethane diisocyanate, 1,4-cyclohexylene diisocyanate, hydrogenated tolylene diisocyanate, and aliphatic diisocyanates such as hexamethylene diisocyanate.

Among these, the alicyclic diisocyanates are preferably used due to their resistance to yellowing and good mechanical properties. These diisocyanates are generally used alone, but two or more of diisocyanates can be used together. And, among the alicyclic diisocyanates, 4,4'-dicyclohexylmethane diisocyanate is the most preferable due to its good balance of mechanical properties and water-vapor permeability of a film to be formed.

The chain extenders used in the present invention are low molecular diols such as ethylene glycol, propylene glycol, diethylene glycol, 1,4-butanediol, 1,6-hexanediol, aliphatic diamines such as ethylenediamine, 1,2-propanediamine, tetramethylenediamine, hexamethylenediamine, alicyclic diamines such as isophoronediamine, 4,4'-dicyclohexylmethanediamine, 3,3'-dimethyl-4,4'-dicyclohexylmethanediamine, 1,4-cyclohexylenediamine, hydrazine hydrate, water, and so on.

Among these compounds, alicyclic diamines are the most preferable due to good stability of polyurethane solution and good heat resistance of a film to be formed. These compounds can be used alone, or two or more of them can be used together. Moreover, the above low molecular diols may be used together in an amount that the mechanical properties and heat-resistance of a film to be produced are not too much lowered. Among those alicyclic diamines, isophoronediamine is the most preferable due to solution stability and good balance of various properties of the film.

The organic solvents having strong dissolving power, for example, dimethylformamide, dimethylacetamide, and dimethyl sulfoxide are suitable for the synthesis of the polyurethane in the present invention. These solvents can be used alone, and also used together with one or more of solvents selected from the aromatic compounds such as toluene and xylene, ketones such as methyl ethyl ketone, acetone and cyclohexanone, esters such as ethyl acetate and butyl acetate, ethers such as tetrahydrofuran and dioxane, alcohols such as methanol and 2-propanol.

The polyurethane resin obtained as described above preferably contains the ethylene oxide unit in an amount of 15 to 60 weight % based on total quantity of the polyurethane. When the ethylene oxide unit is lower than 15 weight %, the water-vapor permeability of the film is not sufficient, and when the ethylene oxide unit is higher than 60 weight %, considerable dimensional change and lowering of physical properties take place by swelling when absorbing water.

Also, if necessary, a catalyst generally used for promoting reactions of urethanization, for example, tertiary amines such as triethylenediamine, organic tin compounds such as dibutyl tin dilaurate, can be used in the reaction.

Moreover, can be previously contained in the polyurethane one or more of hindered phenol type antioxidants, benzophenone type or benzotriazole type ultraviolet absorbing agents, hindered amine type stabilizers, in order to provide better durability. In this case, each additives may be added 0.05 to 3 weight % based on solid parts of polyurethane, and preferably 0.2 to 1 weight % for obtaining better effect. In the polyurethane of the present invention, the above hindered amine type stabilizers are especially effective for avoiding oxidation deterioration upon sterilization treatment and property degradation by hydrolysis.

Either the polyurethane films with porous or non-porous are also available. But it is well known that the polyurethane films with high water-vapor permeability is obtained when making the film porous.

The examples of preparation methods for obtaining porous polyurethane films are as follows;
(1) a wet film-formation method wherein the solution of polyurethane resins are coated on a support, and soluble substances such as solvents are extracted in a coagulating bath.
(2) a method wherein the water in oil-type emulsion is coated on a support, and the porous membrane is obtained from drying by heating.

The non-porous polyurethane films can be obtained from dry film-formation method wherein a solution of polyurethane resin is coated on a support or release paper and dried by heating. By this method, films can be obtained which have stable and reproducible water-vapor permeability, and also have practically sufficient strength, elongation, and durability even if using as single film.

When dry film-formation is carried out, supports used herein are not limited, but polyethylene or polypropylene films, release papers or clothes coated with fluoro or silicone-type releasing agent are preferably used. The above release papers preferably have uniform thickness, because the degree of the water-vapor permeability of the polyurethane films in the present invention is in inverse correlation to the film thickness. The coating method are not specially limited, but either a knife coater or a roll coater can be used. Drying temperature is arbitrarily set up according to the capacity of drying instrument, but it is necessary to select the range of temperature so that insufficient drying or rapid solvent-removal does not occur. The temperature is preferably in the range of 60 to 130° C.

The thickness of the polyurethane films is usually 10 to 200 $\mu$m, preferably 10 to 80 $\mu$m. If the thickness is less than 10 $\mu$m, pin holes are likely to be formed when coating. And also, the films formed are not easy to be handled because of blocking of the films. If the thickness is over 80 $\mu$m, the sufficient water-vapor permeability is difficult to be obtained. Moreover, it is emphasized that the thickness dependence of the water-vapor permeability is small in the polyurethane films of the present invention in comparison with other urethane-type films.

The polyurethane films used in the present invention have high water-vapor permeability which is 2000 g/m$^2$·24 hrs or more, preferably 3000 g/m$^2$·24 hrs or more (by the measurement of JIS Z 0208) in the non-porous films of the thickness of 10 to 80 μm. A film having a value of water-vapor permeability is less than 2000 gm$^2$·24 hrs is not preferable because discomfort is given by steam generated when skin is covered with the film. 100% modulus of the polyurethane film of the present invention is 20 kg/cm$^2$ or more, preferably 30 kg/cm$^2$ or more. If 100% modulus is less than 20 kg/cm$^2$, the films are likely to block each other. On the other hand, if it is more than 80 kg/cm$^2$, they are likely to lack flexibility and reduce water-vapor permeability.

Since the exudation of body fluid is much in the first stage of using a wound covering, the recovery of a wound is slow because of the inhibition of adhesion of the wound covering with the wound by retention of the exudate between a wound and the wound covering, if the wound covering has insufficient water-vapor permeability.

For avoiding slow recovery, it is preferred to provide holes in the wound covering, especially in the polyurethane film, in order to drain the exudate from a wound in the first stage.

It is sufficient for the holes to drain therethrough the exudate from early stage wound. For this purpose, the diameter of the holes is about 0.01 to 1 mm, preferably about 0.1 to 0.7 mm, and the number of the holes is about 2 to 50 cm$^2$, preferably about 5 to 20/cm$^2$.

The holes are formed by sticking needles into the film or punching.

The holes may be blocked after the drain therethrough of the exudate in the early stage. It is rather preferred that the holes are blocked after the drain of the exudate in order to prevent bacteria to penetrate. Therefore, it is also preferred to form slits which are easily opened and closed in place of holes. The slits may be formed in the shapes such as '+', 'V', 'L', 'U', 'I' and '—'. The exudate can be drained through the slits, and thereafter, the slits may be tightly closed to prevent bacteria to penetrate.

When providing the holes which are always open by needles, it is preferable to pre-heat the needles to the melting point or more of the polyurethane film. In this case, it is preferred to add an antibacterial agent into the polyurethane film and the sheet of biopolymeric materials in order to prevent bacteria to penetrate. When using antibacterial agents, the diameter of the holes is preferably within the diameter of the inhibition zone of the antibacterial agent used.

As the biopolymeric material usable in the present invention, collagen, gelatin, alginic acid, chitin, chitosan, fibrin, dextran and polyamino acid may be mentioned. Of the above materials, collagen and chitosan are most preferably used. Collagen mentioned herein may include succinyl collagen, acetyl collagen, methyl collagen, etc.

It is especially preferred that the atelocolagen which is obtained from removing non-helix parts at the end of molecule by treating with a protease except for collagenase is used, since it is near neutral and biocompatible.

Chitosan is also preferred to be used. As chitosan, deacetylated chitin by the action of concentrated alkali is preferably used. The degree of deacetylation is 40% or more, preferably 50% or more.

Moreover, it is also preferred that N-acylchitosan obtained by reaction of chitosan with a carboxylic anhydride is used. The mixture of collagen and chitosan can also be used.

The sheet-formation method of the biopolymeric material is exemplified below.

A solution, dispersion or gel of collagens and/or chitosans are prepared. Then, it is made to be a sponge-like sheet by freeze-drying, or a film by removing solvents after flow-casting on a flat plate.

The thickness of the sheets of biopolymeric material is usually 10 to 100 μm, preferably 10 to 80 μm. When laminate sheets are formed with a polyurethane film, either single sheet or two or more kinds of sheets of biopolymeric material can be piled for use. Also, it is possible to obtain a wound covering having antibacterial effect by incorporating antibacterial agents. As a method for incorporating antibacterial agents into the wound covering of the present invention, a method wherein a sheet of biopolymeric material or a polyurethane film containing a given amount of an antibacterial agent is used, and a method wherein a polyurethane film containing a given amount of an antibacterial agent is provided between the polyurethane film and the sheet of biopolymeric material, thereby forming a three-layered wound covering of polyurethane film/polyurethane film containing antibacterial agent/sheet of biopolymeric material. As the antibaterialagent, sulfa drugs, cephalosporins, penicillins, nalidixic acid and derivative thereof, etc. may be mentioned. The amount of the antibacterial agent used is dependent on the type of the antibacterial agent used, however, it is usually 0.001 to 10% by weight based on the polyurethane film or the sheet of biopolymeric material.

The polyurethane film containing the antibacterial agent can be obtained by dissolving polyurethan resin and an antibacterial agent in a solvent which is capable of dissolving both the resin and agent, mixing the solution well, and then making it into a film.

As the solvent for dissolving both the resin and agent, mixing the solution well, and then making it into a film.

As the solvent for dissolving both the resin and agent, alcohols are usually used. Of the alcohols, those having 5 or less carbon atoms and the boiling point of not higher than 120° C. are preferable, and methanol, ethanol, n-propanol, 2-propanol, n-butanol, sec-butanol, isobutanol and 3- pentanol may be mentioned.

As a method for laminating, a method wherein the sheet of biopolymeric material is laminated on the polyurethane film after swelling the surface of the polyurethane film after swelling the surface of the polyurethane film with an organic solvent which can swell the film surface moderately, for example, alcohols and such as methanol and so on, and dried, and a method wherein the polyurethane film is laminated on the sheet of biopolymeric material after making the solvent described above absorbed in the sheet thereby swelling thee surface of the polyurethane film, and dried.

The wound covering thus obtained is used by contacting the surface of the sheet of biopolymeric material to a wound. With the cure of a wound, the biopolymeric material is taken in a living tissue, therefore, the polyurethane film can be easily peeled off from the sheet without hurting thee surface of a wound after cure.

The present invention is explained more in detail referring the following non-limitative examples.

PREPARATION EXAMPLE 1-4

The preparation of THF-EO random copolymer

Random copolymerization of THF and EO was carried out in an autoclave n the composition shown in Table 1, in the conditions of ordinary pressure, and temperature of 30° C. Ethylene glycol was used as the initiation agent, and boron trifluoride ethyl etherate was used as the acid catalyst. After the completion of copolymerization, the acid catalyst in the product was neutralized with alkali, and the precipitates were filtrated, then dried by blowing dry nitrogen gas at 100° C.

Four kinds of random copolymers of THF and EO (hereinafter referred to as "polyol"), A, B, C, and D are all colorless, and transparent liquids, number-average molecular weight and EOL content being shown in Table 1.

The number-average molecular weight is calculated from the OH value, and EO content is calculated from the amounts of EO charged.

Each polyurethane solution containing antibacterial agent was flow-casted on glass plates provided with spacer, expanded by a glass stick in uniform thickness, and dried for a whole day and night at 80° C. Then, a colorless, and transparent polyurethane film by a dry method was obtained. The film thickness was controlled to be about 30 μm by the spacer. And, in order to investigate the dependency of water-vapor permeability on film thickness, films with various different thickness in the range of 10 to 100 μm were prepared. The films obtained were preserved in a thermohygrostat at 23° C and 60% RH.

Property tests of the polyurethane films were carried out as follows.

Property test of the polyurethane film.

<Measurement of increase rate of dimension by water absorbing>

The increase rate of dimension by water-absorbing was calculated from the measured values of before and after water-absorbing, by soaking polyurethane films of 50 mm×50 mm in water of 23° C for 24 hours.

<Measurement of water-vapor permeability>

The water-vapor permeability was obtained from measurement of the weight using a cup for water-vapor

TABLE 1

|  |  | No. of preparation examples | | | |
|---|---|---|---|---|---|
|  |  | 1 | 2 | 3 | 4 (comparative example) |
|  |  | Composition of polyols | | | |
|  |  | A | B | C | D |
| Components of polyol (Weight parts) | Ethylene glycol | 28.2 | 17.2 | 13.4 | 15.5 |
|  | THF | 236 | 241.4 | 194.6 | 72.7 |
|  | E O | 236 | 241.4 | 291.9 | 411.8 |
|  | boron trifluoride ethyl etherate | 32.3 | 19.7 | 15.3 | 17.8 |
| Number-average molecular weight | | 1100 | 1800 | 2300 | 2000 |
| EO content (weight %) | | 50 | 50 | 60 | 85 |

PREPARATION EXAMPLES 5-8

Preparation of polyurethane film a) Preparation of polyurethane solution

A urethane prepolymer having an isocyanate group at the end of the molecular chain thereof was obtained by the reaction of 4,4'-dicyclohexylmethane diisocyanate and each of the polyol A, B, C, and D obtained in preparation examples 1-4 in the composition as shown in Table 2 in a flask under an atmosphere of dry nitrogen at 100° C for 6 hours. After this, chain-extending reaction of each of the above prepolymers was carried out in dimethylformamide using isophorone diamine as the chain extender for 2 hours at 30° C. Then, each polyurethane solution which was colorless, transparent, and viscous, was obtained. The solid content of each of the solution was 25 weight %. The viscosities of the solutions at 25° C. were 35,000 cps, 20,000 cps, 15,000 cps, 16,000 cps respectively.

b) Formation of polyurethane film

Polyurethane resin was precipitated by dropping each of the above solutions into water. After filtrating and drying the solid polyurethane, each methanol solution which contains 15% by weight of polyurethane resin was prepared. Then, silver sulfadiazine as antibacterial agent was added in an amount of 30 weight % based on the polyurethane resin, and the mixture was stirred to make it uniform.

permeability measurement under the conditions of 40° C. and 90% RH according to JIS Z.0208.

<Oxidation resistance test>

The influence to mechanical properties by oxidative deterioration was examined by irradiating γ ray of exposure dose of 2.5 Mrad in a dose rate of $10^6$ rad/hr in air, supposing sterilization treatment by radiation.

<Hydrolysis resistance test>

Hydrolysis resistance was evaluated by measuring mechanical properties after exposing the polyurethane films under the atmosphere of 70° C, and 95% RH for 3 weeks.

PREPARATION EXAMPLE 9

Preparation of polyurethane film

A hindered amine type stabilizing agent Tinuvin ® 622 LD (sold from Chiba-Geigy Co.) was added to the polyurethane solution obtained in preparation example 6 in an amount of 0.5 weight % based on the polyurethane contained. Then, by the same method as in preparation example 6, a polyurethane film was prepared, and tests were carried out.

As shown in Table 4, the properties of the polyurethane film were remarkably improved in comparison with the film of the preparation example 6 which does not contain Tinuvin ® 622 LD, for example, in oxidative deterioration when irradiating γ ray, lowering of mechanical properties by hydrolysis.

TABLE 2

|  |  | \multicolumn{5}{c}{No. of preparation example} |
|---|---|---|---|---|---|---|

| | | 5 | 6 | 7 | 8 (Comparative example) | 9 |
|---|---|---|---|---|---|---|
| Composition of polyurethane (Weight parts) | Polyol A | 305.7 | | | | |
| | Polyol B | | 359.6 | | | 359.6 |
| | Polyol C | | | 383.0 | | |
| | Polyol D | | | | 370.0 | |
| | 4,4'-dicyclohexylmethane diisocyanate | 145.6 | 104.7 | 87.3 | 96.9 | 104.7 |
| | Isophorone diamine | 48.7 | 35.7 | 29.7 | 33.1 | 35.7 |
| Additives | Tinuvin ® 622LD | — | — | — | — | 2.5 0.5 wt % based on polyurethane |

PREPARATION EXAMPLES 10–13

Preparation of polyurethane film

Each of polyurethane solutions was prepared in the composition shown in Table 3. In preparation examples 10–12 wherein 4,4-dicyclohexylmethane diisocyanate and isophorone diamine were used, the polyurethane solutions were prepared in the same manner as in preparation examples 5–8. The solid contents and viscosities at 25° C of the solutions were 25 weight % and 20,000 cps in preparation example 10, 20 weight % and 23,000 cps in preparation example 11, 20 weight % and 18,000 cps in preparation example 12, respectively.

In preparation example 13, urethane prepolymer was obtained by the reaction of 4,4'-diphenylmethane diisocyanate and polyol B in a flask under an atmosphere of dry nitrogen at 80° C for 4 hours. Then, chain-extending reaction of the above prepolymer was carried out in dimethylformamide at 80° C for 6 hours using 1,4-butanediol as the chain extender in the presence of 100 ppm of dibutyl tin dilaurate. The solid content was 25 weight % and the viscosity at 25° C was 19000 cps.

The formation of the polyurethane film and tests of properties were carried out in the same manner as in preparation examples 5–8.

The properties of the polyurethane film of preparation examples 10 and 11 are shown in Table 4.

TABLE 3

| | | \multicolumn{4}{c}{No. of preparation examples} |
|---|---|---|---|---|---|

| | | 10 | 11 | 12 (comparative example) | 13 |
|---|---|---|---|---|---|
| Composition of polyurethanes (weight parts) | Polyol PTMG 2000 (note) | 330.5 | 305.8 | 369.8 | 310.3 |
| | 4,4'-dicyclohexylmethane diisocyanate | 120.3 | 133.5 | 96.9 | |
| | 4,4'-diphenylmethane diisocyanate | | | | 150.9 |
| | Isophorone diamine | 49.2 | 60.7 | 33.3 | |
| | 1,4-butanediol | | | | 38.8 |

(note)
Polytetramethylene ether glycol having a number-average molecular weight 2000 (sold from Mitsubishi Kasei Corporation)

TABLE 4

| | \multicolumn{4}{c}{No. of preparation examples} |
|---|---|---|---|---|

| | 6 | 9 (Stabilizer was added) | 10 | 11 |
|---|---|---|---|---|
| EO contents in polyurethane (wt %) | 36 | 36 | 33 | 31 |
| Increase rate of dimension by water-absorbing (%) | 2.0 | 2.0 | 1.6 | 1.3 |
| Water-vapor permeability (g/m².24 hr) Film thickness | | | | |
| 10 μm | 6700 | 6700 | 6200 | 5500 |
| 20 μm | 5700 | 5700 | 4800 | 4300 |
| 30 μm | 4400 | 4400 | 3800 | 3500 |
| 50 μm | 3150 | 3150 | 2800 | 2600 |
| 80 μm | 2200 | 2200 | 2000 | 1900 |
| Mechanical properties | | | | |
| 100% modulus (kg/cm²) | 33 | 34 | 49 | 66 |
| Tensile strength (kg/cm²) | 382 | 390 | 457 | 477 |
| Elongation (%) | 676 | 668 | 640 | 606 |
| Oxidation resistance 100% modulus retention (%) | 75 | 94 | — | — |
| Hydrolysis resistance Tensile strength retention (%) | 7 | 60 | — | — |

EXAMPLE 1–6

A laminate sheet of a collagen sheet and a polyurethane film was prepared as follows. A uniform foaming solution was prepared by stirring a solution containing 1% by weight of atelocollagen, which was adjusted to pH 4 with hydrochloric acid in a homogenizer at a rate of 1500 rpm for 5 minutes.

It was flow-casted to a thickness of 1 to 2 mm. Then, the atelocollagen solution was neutralized by allowing it to stand in an atmosphere of ammonia for 30 minutes to be gelatinized. Then, a sponge-like collagen sheet was obtained by freeze-drying atelocollagen gel in a freeze-drier controlled at −30° C. This collagen sheet was made water-insoluble by cross-linking caused by UV irradiation. A small amount of methanol was absorbed into the collagen sheet. Then, a laminate sheet of the sponge-like collagen sheet and the polyurethane film was obtained by laminating the collagen sheet with the polyurethane film of thickness of 30 μm, obtained in preparation examples 5–7, 10, 11 or 13, and drying. Then, a porous laminate sheet was obtained by forming holes with a frog.

The sheet was sterilized with gaseous ethylene oxide, and was applied to the tests.

A wound (diameter: 35 mm) of full thickness skin defect was made surgically at the abdominal part of a rat (SP rat of 6 to 8 week-old), and a stainless ring of 0.4 mmo was sutured (16 stitches). The laminate sheet obtained above was put on the ring, and moisture-retentive pad and sanitary cotton were placed on it, then bandaged with an elastic band. The biocompatibility and regeneration of the dermis were histologically examined after one week and two weeks. And the effect of the laminate sheet was evaluated. These result are shown in Table 5. Curing effect is good in all the laminate sheets, and it has been found that the laminate sheet of the present invention is suitable for a wound covering.

EXAMPLE 7

A laminate sheet of an alginic acid sheet and a polyurethane film was prepared as follows. The uniform forming dispersion was obtained by dispersing sodium alginate (sold from Kimitsu Kagaku Industry Co., Ltd.) in water in a concentration of 2% and stirring the dispersion by using a homogenizer at a rate of 1500 rpm for 5 minutes.

It was flow-casted to a thickness of 1 to 2 mm, and the sponge-like sheet of sodium alginate was obtained by freeze-drying at $-80°$ C. Then, after spraying methanol on the sodium alginate sheet, the polyurethane film of the thickness of 30 $\mu$m obtained in preparation example 10 was laminated thereon, and dried to obtain a laminate sheet. A porous laminate sheet was obtained by forming holes by a frog. This was applied to the tests after sterilization treatment by gaseous ethylene oxide. The applicability of this laminate sheet as a wound covering was examined by the experiment similar to examples 1–6. As seen from the results in Table 5, the laminate sheet was found to be effective as a wound covering in the same manner as in the case of examples 1–6.

EXAMPLE 8

A laminate sheet of a collagen-chitosan sheet and a polyurethane film was prepared as follows.

Into 0.5 liter of a 2% aqueous acetic acid solution, were dissolved 9 g of N-succinylchitosan having a degree of succinylation of 50% and 1 g of atelocollagen, and then, 1 liter of methanol was added into the solution.

The aqueous methanol-acetic acid solution containing N-succinylchitosan and atelocollagen was added with 12 g of acetic anhydride, mixed well and allowed to stand for 10 hours at room temperature. The solution was washed thoroughly with water to remove acetic acid and methanol, thereby obtaining 180 g of hydrated gel of acetylated chitosan-collagen.

The thus prepared hydrated gel was immersed in 3 liters of methanol, quick-freezed by adding dry ice and then freeze-dried in vacuo to obtain 10 g of sponge of acetylated chitosan-collagen. The sponge was sliced into a piece of 2mm thickness, followed by irradiation of 5 Mrad $\gamma$-ray to cross-link the acetylated chitosan-collagen. The cross-linked sponge was immersed in methanol, then after removing off the majority of methanol, the polyurethane film of thickness of 25 $\mu$m obtained in preparation example 7 was laminated thereon and air dried at room temperature.

The thus obtained laminate sheet of the acetylated chitosan-collagen was provided with holes of diameter of 0.3 mm in 10 holes per 1 cm$^2$ area by using a flog.

The porous laminate sheet was sterilized with gaseous ethylene oxide, and applied to the same tests as in examples 1 to 7.

The results are shown in Table 5.

TABLE 5

| | No. of examples | | | | | | | |
|---|---|---|---|---|---|---|---|---|
| | 1 | 2 | 3 | 4 | 5 | 6 | 7 | 8 |
| | Polyurethane film | | | | | | | |
| | Preparation example-5 | Preparation example-6 | Preparation example-7 | Preparation example-10 | Preparation example-11 | Preparation example-13 | Preparation example-10 | Preparation example-7 |
| EO contents in polyurethane (weight %) | 31 | 36 | 46 | 33 | 31 | 31 | 33 | 46 |
| Properties of polyurethane films — Increase rate of dimension by water-absorbing (%) | 1.2 | 2.0 | 3.0 | 1.6 | 1.3 | 1.0 | 1.3 | 3.0 |
| Water-vapor permeability (g/m$^2$·24 hr) | 3500 | 4400 | 4800 | 3800 | 3500 | 3400 | 3800 | 4800 |
| Sheet of biopolymeric material | Collagen sheet | Collagen sheet | Collagen sheet | Collagen sheet | Collagen sheet | Collagen sheet | Alginic acid sheet | Chitosan-Collagen sheet |
| Curing effect in rats | Good | Good | Good | Good | Good | Good | Good | Good |

COMPARATIVE EXAMPLES 1–2

Two porous laminate sheets were obtained from the sponge-like collagen sheet and the polyurethane films of thickness of 30 $\mu$m obtained in the preparation examples 8 and 12, in the same manner as in examples 1–6. The applicability of these laminate sheet as a wound covering was examined. The results are shown in Table 6.

In comparative example 1, water-vapor permeability of the polyurethane film was high, but adhesion between the laminate sheet and the wound was bad by swelling of the film due to water-absorbing. In comparative example 2, curing effect was recognized, but the degree of the effect was insufficient compared with examples 1–6. This is because water-vapor permeability of the polyurethane film was low.

TABLE 6

| | | No. of comparative examples | |
|---|---|---|---|
| | | 1 | 2 |
| | | Polyurethane film | |
| | | Preparation example - 8 | Preparation example - 12 |
| EO contents in polyurethane (weight %) | | 63 | 0 |
| Properties of urethane films | Increase rate of dimension by water-absorbing (%) | 15.0 | 0.7 |
| | Water-vapor permeability | 6000 | 2300 |

TABLE 6-continued

| | No. of comparative examples | |
|---|---|---|
| | 1 | 2 |
| | Polyurethane film | |
| | Preparation example - 8 | Preparation example - 12 |
| (g/m².24 hr) Sheet of biopolymeric material | Collagen sheet | Collagen sheet |
| Curing effect | Bad adhesion by swelling, improper. | Effect showed, but inferior to examples. |

EXAMPLE 9

A laminate sheet of a plyurethane film and a collagen sheet containing an antibacterial agent was prepared as follow.

A foaming-dispersion was prepared by adding silver sulfadiazine into a 1% atelocollagen solution, which was adjusted to pH 4 with hydrochloric acid, in such an amount that the concentration of silver sulfadiazine was 1500 ppm, then stirring the solution by using a homogenizer at a rate of 1500 rpm for 5 min.

It was flow-casted to a thickness of 1 to 2 mm. Then, the atelocollagen solution was neutralized by allowing it to stand in an atmosphere of ammonia for 30 min to be gelatinized. Then, the atelocollagen gel was freeze dried in a freeze-drier at $-30°$ C to obtain a sponge-like collagen sheet. The collagen sheet was made water-insoluble by cross-linking caused by UV irradiation.

A small amount of methanol was absorbed in the collagen sheet. Then, the polyurethane film of thickness of 30 $\mu$m obtained in preparation example 5 was laminated on the collagen sheet to obtain a laminate sheet of the polyurethane film and the collagen sheet containing an antibacterial agent. Then, a porous laminate sheet was obtained by forming holes by using a frog.

After sterilization treatment with gaseous ethylene oxide, the sheet thus obtained was applied to the following test.

*Pseudomonas aerucinosa* was inoculated in an agar culture medium in a density of $10^7$ P.a/cm². Then, the laminate sheet sterilized above was placed thereon, and the number of the bacteria under the sheet was measured after one day.

As a comparison, the same experiment was repeated using a chitin-nonwoven fabric and a pig skin.

After one day, *Pseudomonas aerucinosa* under the sheet containing an antibacterial agent has been disinfected completely, whereas, under the chitin-nonwoven fabric and the pig skin, *Pseudomonas aeruginosa* proliferated and the number of the bacteria was $10^9$ P.a/cm².

What is claimed is:

1. A laminate wound covering comprising a sheet of biopolymeric material selected from the group consisting of collagen, gelatin, alginic acid, chitin, chitosan, fibrin, dextran and polyamino acids, for contacting said wound and a film of a polyurethane resin in contact with said biopolymeric material sheet having a water-vapor permeability of 2,000 g/m².24 hrs. or more which is obtained by reacting a diisocyanate and a random copolymer of tetrahydrofuran and ethylene oxide to produce a urethane prepolymer, and extending the molecular chain of said prepolymer by using a chain extender, said random copolymer having 20 to 80% by weight of the ethylene oxide unit in the molecular chain thereof and having a number-average molecular weight of 800 to 3000.

2. A wound covering according to claim 1, wherein said polyurethane film or said sheet of a biopolymeric material contains an antibacterial agent.

3. A wound covering according to claim 1, wherein said random copolymer has 30 to 70% by weight of the ethylene oxide unit in the molecular chain thereof.

4. A wound covering according to claim 1, wherein said number-average molecular weight of said random copolymer is 1000 to 2500.

5. A wound covering according to claim 1, wherein said diisocyanate is alicyclic diisocyanate.

6. A wound covering according to claim 5, wherein said alicyclic diisocyanate is a member selected from the group consisting of isophorone diisocyanate, 4,4'-dicyclohexylmethane diisocyanate, 1,4-cyclohexylene diisocyanate, and hydrogenated tolylene diisocyanates.

7. A wound covering according to claim 6, wherein said alicyclic diisocyanate is 4,4-dicyclohexylmethane diisocyanate.

8. A wound covering according to claim 1, wherein said chain extender is alicyclic diamine.

9. A wound covering according to claim 8, wherein said alicyclic diamine is a member selected from the group consisting of isophorone diamine, 4,4'-dicyclohexylmethane diamine, 3,3'-dimethyl-4,4'-dicyclohexylmethane diamine, and 1,4-cyclohexylene diamine.

10. A wound covering according to claim 9, wherein said alicyclic diamine is isophorone diamine.

11. A wound covering according to claim 1, wherein the thickness of said polyurethane film is 10 to 80 $\mu$m.

12. A wound covering according to claim 1, wherein 100% modulus of said polyurethane film is 20 kg/cm² to 80 kg/cm.

13. A wound covering according to claim 1, wherein the thickness of said polyurethane film is 10 to 80 $\mu$m, water-vapor permeability of said film is 2,000g/m².24 hrs to 80 kg/cm, and 100% modulus of said film is 20 kg cm² or more.

* * * * *